United States Patent
Newton et al.

(10) Patent No.: US 6,743,445 B2
(45) Date of Patent: Jun. 1, 2004

(54) LOW TEMPERATURE COATINGS

(75) Inventors: John Michael Newton, London (GB); Chuei Wuei Leong, Kedah (MY)

(73) Assignee: BTG International Limited, London (GB)

(*) Notice: Subject to any disclaimer, the term of this patent is extended or adjusted under 35 U.S.C. 154(b) by 71 days.

(21) Appl. No.: 10/137,702

(22) Filed: May 3, 2002

(65) Prior Publication Data

US 2003/0077326 A1 Apr. 24, 2003

Related U.S. Application Data

(63) Continuation of application No. 09/534,996, filed on Mar. 27, 2000, now abandoned, which is a continuation of application No. PCT/GB98/03428, filed on Nov. 13, 1998.

(51) Int. Cl.[7] .............................. A61K 9/36; A61K 9/28

(52) U.S. Cl. ...................... 424/480; 424/400; 424/451; 424/464; 424/468; 424/474; 424/475; 424/480; 424/484; 424/489; 424/490; 514/964

(58) Field of Search .................................. 424/400, 451, 424/464, 468, 472, 474, 475, 479, 480, 489

(56) References Cited

U.S. PATENT DOCUMENTS

| | | |
|---|---|---|
| 2,196,768 A | 4/1940 | Hiatt |
| 4,755,397 A | 7/1988 | Eden et al. |
| 5,108,758 A * | 4/1992 | Allwood et al. ............. 424/468 |
| 5,294,448 A * | 3/1994 | Ring et al. .................. 424/497 |
| 5,639,476 A | 6/1997 | Oshlack et al. |
| 5,656,292 A | 8/1997 | Urtti et al. |
| 5,780,057 A | 7/1998 | Conte et al. |
| 5,811,388 A | 9/1998 | Friend et al. |
| 5,858,412 A | 1/1999 | Staniforth et al. |
| 6,024,982 A * | 2/2000 | Oshlack et al. ............. 424/476 |

FOREIGN PATENT DOCUMENTS

| | | |
|---|---|---|
| EP | 0 343 993 | 11/1989 |
| GB | 2220 350 | 1/1990 |
| WO | 89/00601 | 1/1989 |

OTHER PUBLICATIONS

Milojevic et al, Amylose as a coating for drug delivery to the colon: preparation . . . , Journal of Controlled Release, vol. 38, pp. 75–84 (1996).

Milojevic et al, "Amylose as a coating for drug delivery to the colon: preparation . . . ," Journal of Controlled Release, vol. 38, pp. 85–94 (1996).

Cummings et al, "In vivo studies of amylose– and ethylcellulose–coated . . . ," Journal of Controlled Release, vol. 40, pp. 123–131 (1996).

Yang et al; "The effect of product bed temperature on the microstructure of Aquacoat–based controlled–release coatings; Int'l Journal of Pharmaceutics", 60 (1990) 109–124.

Bodmeier et al; "The effect of curing on drug release and morphological properties of ethylcellulose pseudolatex–coated beads"; Drug Development and Industrial Pharmacy, 20(9), 1517–1533 (1994).

Mehta, et al; "Evaluation of fluid–bed processes for enteric coating systems"; Pharmaceutical Technology, Apr. 1986, pp 46, 48–56.

(List continued on next page.)

Primary Examiner—Thurman K. Page
Assistant Examiner—Charesse Evans
(74) Attorney, Agent, or Firm—Nixon & Vanderhye

(57) ABSTRACT

A method of coating an active material is provided. The method comprises contacting an active material with a film-forming composition comprising an aqueous dispersion of an amylose-alcohol complex, an insoluble film-forming polymer and a plasticiser at a temperature of less than 60° C. The method finds particular application in the preparation of dosage forms comprising active materials that are unstable at temperatures in excess of 60° C. The compositions prepared in accordance with the method can be used to deliver an active material to the colon.

17 Claims, 6 Drawing Sheets

Figure 1:
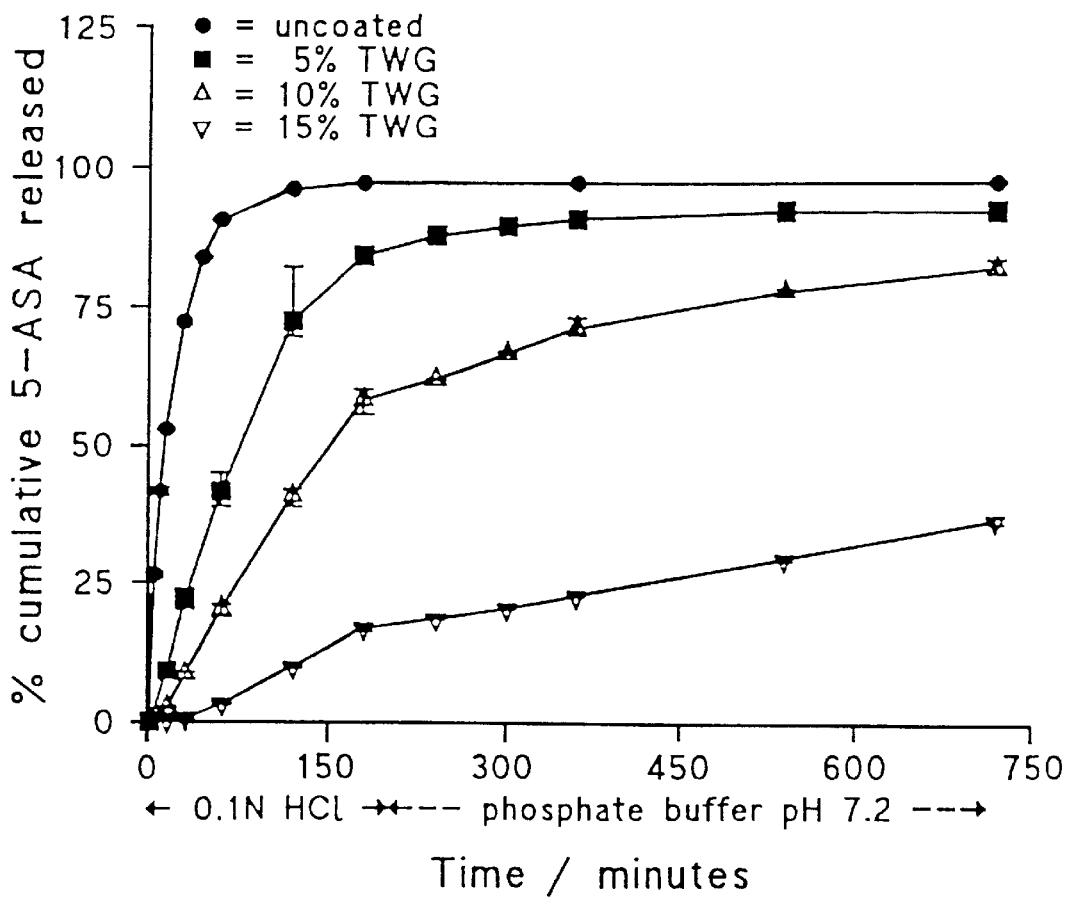

Effect of coat thickness on the dissolution results of AG1 pellets coated with Surelease EA7100:amylose (2.5:1) at 35°C

OTHER PUBLICATIONS

Ghebre–Sellassie et al; "Characterization of a new water–based coating for modified–release preparations"; Pharmaceutical Technology, Sep. 1988, pp 96–106.

Jones, David M.; "Factors to consider in fluid–bed processing"; Pharmaceutical Technology, Apr. 1985, pp 50–62.

Lippold, et al; "Parameters controlling drug release from pellets coated with aqueous ethyl cellulose dispersion"; International Journal of Pharmaceutics, 54 (1989) 15–25.

Porter, Stuart C.; "Controlled–release film coatings based on ethylcellulose"; Drug Development and Industrial Pharmacy, 15(10), 1495–1521 (1989).

Muhammad, et al; "Modifying the release properties of eudragit® L30D"; Drug Development and Industrial Pharmacy, 17(18), 2497–2509 (1991).

Arwidsson, et al; "Properties of ethyl cellulose films for extended release, II. Influence of plasticizer content and coalescence conditions when using aqueous dispersions"; Acta Pharm. Nord. 3(2) 65–70 (1991).

Arwidsson, et al; "Properties of ethyl cellulose films for extended release, III. Influence of process factor when using aqueous dispersions"; Acta Pharm. Nord. 3(4) 223–228 (1991).

Lehmann et al; "Coating of tablets and small particles with acrylic resins by fluid bed technology"; Int. J. Pharm. Tech. & Prod. Mfr., 2(4) 31–43 (1981).

Manufacturing Chemist Mar. 1986; "Films from water–based colloidal dispersions"; pp 55–59.

Goodhart, et al; "An evaluation of aqueous film–forming dispersions for controlled release"; Pharmaceutical Technology, Apr. 1984.

Donbrow et al; "Zero order drug delivery from double–layered porous films: release rate . . . polyethylene glycol mixtures"; J. Pharm. Pharmacol. 1980, 32: 463–470.

Bindsschaedler, et al; notions théoriques sur la formation . . . et application à l'enrobage; Labo–Pharma—Probl. Tech. 31, n° 331, Mai 1983, pp 389–394.

Milojević Snežana; "Amylose coated pellets for colon—specific drug delivery"; The School of Pharmacy, University of London, Oct. 1993.

Porter, Stuart C.; Chapter 8, The Use of Opadry, Coateric, and Surelease in the Aqueous Film Coating of Pharmaceutical Oral Dosage Forms; From Aqueous Polymeric Coating for Pharmaceutical Dosage Forms (1989); C.R. Steuernagel et al, NY& Basel, Mercer Dekker Inc., pp 317–363.

Mehta, Atul M.; "Chapter 6, Processing and Equipment Considerations for Aqueous Coatings"; From Aqueous Polymeric Coating for Pharmaceutical Dosage Forms (1989); C.R. Steuernagel et al, NY& Basel, Mercer Dekker Inc., pp 267–303.

Lehmann, Klaus O.R.; "Chapter 4, Chemistry and Application Properties of Polymethacrylate Coating Systems"; Mainly background, From Aqueous Polymeric Coating for Pharmaceutical Dosage Forms (1989); C.R. Steuernagel et al, NY& Basel, Mercer Dekker Inc., pp 153–245.

Steuernagel, C.R.; "Chapter 1, Latex Emulsions for Controlled Drug Delivery"; Nov. 4, 2002—Of background interest only, From Aqueous Polymeric Coating for Pharmaceutical Dosage Forms (1989); C.R. Steuernagel et al, NY& Basel, Mercer Dekker Inc., pp1–61.

* cited by examiner

LOW TEMPERATURE COATINGS

This application is a continuation of application Ser. No. 09/534,996, filed Mar. 27, 2000, now abandoned, the entire content of which is hereby incorporated by reference in this application. Priority is hereby claimed under 35 USC 119 based on the following foreign application: continuation of PCT/GB98/03428, filed Nov. 13, 1998.

The present invention relates to controlled, usually delayed release formulations, especially compositions that are suitable for delivering an active ingredient to the colon.

Compositions comprising amylose have been used in the preparation of dosage forms that can be used to deliver an active ingredient to the colon. The preparation of such dosage forms is described in U.S. Pat. No. 5,294,448 and involves contacting an active ingredient with a solution or dispersion of amylose formed from an aqueous amylose-butanol complex at a temperature in excess of 60° C. to form a film and drying that film. Temperatures in excess of 60° C. are considered to be essential in order to maintain or melt respectively the amylose in the solution or dispersion that comprises the film-forming composition. When the compositions are cooled the amylose in the films formed therefrom is in the glassy state.

Glassy amylose is one of the amorphous forms of amylose, the other being rubbery amylose. The rate of cooling and drying of the amylose film is considered to be important in the preparation of amylose films. If the rate of cooling is too low, crystalline regions of amylose are formed. If the quantity of water within the film exceeds a certain amount, the amylose may be formed in the rubbery form. Both crystalline and rubbery amylose are not digestible in the Gastro-Intestinal (GI) tract and are not considered to be suitable for the preparation of formulations for use in the delivery of an active material to the colon. In contrast glassy amylose has been found to be resistant to attack by the α-amylases present in the small intestine but is degraded by the microflora present in the colon. These properties mean that it is particularly suitable for the preparation of dosage forms that can be used to deliver an active ingredient to the colon.

However, coats or films comprising purely glassy amylose have been found to swell in an aqueous environment and these swollen films are unable to retain their structural integrity when subject to mechanical stresses such as those experienced by the dosage form on its passage through the GI tract. Films or coats comprising amylose only are therefore unsuitable for the preparation of dosage forms for use in colonic delivery.

In order to overcome the disadvantages associated with films comprising amylose only, mixed compositions comprising amylose and a film-forming polymer have been prepared. See for example U.S. Pat. No. 5,294,488. The presence of a film-forming polymer prevents or limits the degree to which the amylose swells and confers some structural integrity on the film during its passage through the GI tract. Further ingredients such as water-soluble plasticisers may be added to the composition to assist in the formation of the final film or coat.

As with the preparation of "amylose only" films, the preparation of films from the mixed film-forming composition required that the composition be contacted with the active ingredient at a temperature in excess of 60° C. As before, this was in order to ensure that the amylose present in the composition was either completely solvated or in a melted form prior to the coating step. Upon drying the film, the amylose is preferably present in the glassy state. Coats or films comprising rubbery amylose may be formed but require the presence of porosity enhances in order to facilitate release of active material.

The formation of dosage forms in accordance with the method described in U.S. Pat. No. 5,294,448 has been found to be completely satisfactory for the preparation of dosage forms in which the active material is not temperature sensitive, but cannot be used for active materials that are thermolabile at temperatures above 60° C. There is, therefore, a need for a method of coating, active materials for the preparation of dosage forms in which the active material is thermolabile above 60° C. The present invention addresses, at least in part, that problem.

The present inventors have surprisingly found that a film-forming composition can be prepared which can be used to coat active materials at temperatures of less than 60° C. Surprisingly the structural integrity of the films formed is substantially retained during their passage through the GI tract. By retention of structural integrity, it should be understood that the coat or film does not substantially swell and is retained by the active material on its passage through the GI tract. However, parts of the film may be lost, weakened or degraded at certain points in the GI tract as will be described herein below. These films are also unexpectedly resistant to digestion in both the stomach and the small intestine, but are degraded by the microflora present in the colon.

A first aspect of the invention provides a method of coating an active material or a formulation containing an active material comprising the steps of contacting an active material or formulation containing it at a temperature of less than 60° C. with a film-forming composition comprising an aqueous dispersion of an amylose-alcohol complex, an insoluble film-forming polymer and a plasticiser, coating being carried out at a temperature of less than 60° C. The coating step may suitably be carried out at a temperature of between 5 and 50° C., preferably between 20 and 40° C., more preferably between 30 and 40° C. and especially between 35 and 37° C. As indicated above, coatings formed according to the first aspect of the invention are surprisingly able to retain their structural integrity during their passage through the GI tract. They are substantially resistant to digestion in both the stomach and the small intestine but are degraded by the microflora present in the colon.

By the term "film-forming" it is to be understood that the composition is able to form a coat or a film upon contact with the active material (or a formulation containing the active material) that solidifies upon drying. The structural integrity of the film is substantially retained during its passage through the GI tract. The film or coat is also able to substantially resist digestion in the stomach and small intestine but is degraded by the microflora of the colon.

It is also believed that the films or coatings formed using the method of the present invention comprise substantially homogeneous mixtures of amylose and an insoluble cellulosic or acrylic polymer. The term homogeneous includes films comprising distinct regions of amylose randomly dispersed in an insoluble cellulosic polymer matrix as well as films in which the dispersion is such that the regions of amylose are indistinguishable from an insoluble cellulosic polymer matrix material for example.

The term "active material" applies to any material which is or may be sensitive to temperatures above low ambient, for example 20 to 40° C., but also includes materials that are not degraded at temperatures outside this range. The active material could, for example, be a foodstuff or a pharmaceutical. It particularly includes any compound or composition useful in human or veterinary medicine, in therapy or diagnosis.

Preferred active materials include therapeutically active ingredients that find application in treating diseases of the colon or diseases the therapeutic management of which is best effected via the colon. Such diseases include, but are not limited to, cancer of the colon, irritable bowel syndrome (IBS) and Crohn's disease.

It will be appreciated that the active material may be mixed with other carrier materials suitable to a particular use. Thus, particularly for therapeutic use, the active material will often be mixed with one or more of a bulking agent and a lubricant, for example lactose and magnesium stearate, respectively. Dosages of active materials for therapeutic use will be as disclosed in the literature, for example in the ABPI data sheet compendium, or may sometimes be less owing to the more efficient delivery of the material. The active in material may be used together with one or more additional active materials.

The invention also includes a the coating of a formulation containing an active material e.g. a dosage form containing a coated or uncoated active material such as, pellets, capsules or tablets.

The active material, either alone or in admixture with a carrier, is coated with a coating material at temperatures that do not destroy the integrity of the substrate but are greater than the minimum film-forming temperature for the composition The term "dosage form" should be understood to include any solid dosage form that may be administered to a human or animal patient or that may be used in an agricultural or industrial application, without limitation. Examples of suitable dosage forms include tablets, pellets and capsules.

In addition to their value in achieving a delayed release of therapeutic agents, particularly in their delivery to the colon as discussed above, the compositions of the invention are useful in diagnosis, for example in delivering agents such as contrast media to the colon in connection with X-ray and NMR imaging techniques. An alternative diagnostic area lies in the delivery of potentially allergenic foodstuff components to the colon for the diagnosis of allergies.

By the term "insoluble polymer" it is to be understood to mean that the polymers present in the film-forming composition should be water-insoluble as well as insoluble in aqueous acidic and alkaline media. Thus the solubility of the film-forming polymer in water at room temperature should be less than 10% w/v. The level of solubility in aqueous acidic media at pH 1 should be less than 1% w/v and in aqueous alkaline media at a pH of 7.2 should be less than 1% w/v. Any pharmaceutically or agriculturally acceptable insoluble polymer may be used in the preparation of the film-forming compositions of the invention. Preferred film-forming polymers include water-insoluble cellulosic or acrylic polymers. Shellac may also be used. Mixtures of different polymers may be used. The use of ethyl cellulose as a film-forming polymer is especially preferred.

The term "acrylic polymer" includes both acrylate and methacrylate polymers and especially co-polymers thereof, the esterifying groups in these polymers being of various types, for example $C_{1-18}$ alkyl groups. Preferred forms of acrylate polymer are those marketed under the TradeMark Eudragit, particularly Eudragit RL and RS whose degradation is independent of pH.

A preferred molecular weight range for the film-forming cellulose materials is 42,000 to 280,000 g/mol (or daltons) and for the film-forming acrylic polymer materials is 150,000 to 250,000 g/mol (or daltons) but materials with molecular weights outside these ranges, for example of a higher molecular weight, can be used where appropriate.

The degradation of the cellulose materials in vivo is in general not pH dependent and it is preferred that this is also true for the acrylate materials. This may be achieved by the selection of appropriate forms of side chain on the main polymer chain, in particular of side chains that have a low negative charge or preferably which are uncharged, as opposed to those having a positive charge. Preferred forms of acrylate polymers are those marketed by Dumas (UK) Limited of Tunbridge Wells under the TradeMark Eudragit, particularly the materials Eudragit L whose degradation is independent of pH. A preferred cellulose polymer, ethyl cellulose, is marketed by the Dow Chemical Company and Shinetsu Chemical Products under the TradeMark Ethocel.

Other preferred forms of cellulosic polymers include ethyl cellulose pseudolatex solutions, which are sold under the TradeMarks Surelease® and Aquacoat®.

Surelease® is prepared by forming a homogeneous melt of ethyl cellulose (20 cPs, USNF), the plasticiser dibutyl sebacate and an oleic acid stabiliser and dispersing said melt in ammoniated water to give a dispersion containing 25% w/w solids. Hydrogenated coconut oil may also be used as a plasticiser instead of or in addition to dibutyl sebacate. The plasticiser (dibutyl sebacate and/or hydrogenated coconut oil) is generally present in a total amount comprising 20 to 24% by weight of the ethyl cellulose polymer, preferably 21 to 22% by weight. The process of adding a plasticiser to a film-forming polymer prior to dispersion in water is known as pre-plasticisation and the term "pre-plasticised polymer" should be understood accordingly. Plasticisation may also be achieved by the addition of a plasticiser to the aqueous dispersion of the insoluble polymer.

Aquacoat® is manufactured by dissolving ethyl cellulose (10 cPS, premium grade) in a water immiscible solvent; emulsifying in water in the presence of an anionic surfactant and a stabiliser; homogenising the crude emulsion and removing the organic solvent to give an aqueous pseudolatex dispersion containing 30% w/w solids. The commercially available Aquacoat® dispersion contains no plasticiser.

Formation of an aqueous dispersion of an amylose-alcohol complex is well known and is described in U.S. Pat. No. 5,294,448 and also by Milojeric et al, in J. Controlled Release, 38 (1996) 75–84 and requires the precipitation from solution of amylose through the formation of an amylose-alcohol complex. Any $C_{3-6}$ alcohol may be used to precipitate the amylose. The use of butan-1-ol to precipitate amylose from solution is particularly preferred.

The dosage forms prepared in accordance with the first aspect of the invention are dried at a temperature of between 5 and 40° C., preferably 20 to 40° C. and especially between 33 and 37° C. over a period of between 0 and 2 hours, preferably between ½ and 1 hour and especially for between ½ and ¾ hour. The temperature at which the dosage formed is dried will depend, in part, upon the temperature at which the coating was carried out and is preferably no higher than the coating temperature. The time for which the dosage forms are dried will depend upon factors such as the initial concentration of the film forming composition and the drying temperature selected. Long drying times should be avoided as these may result in crystalline regions within the final film. Shorter drying times ensure that the amylose is retained in the amorphous form in the final form, preferably in the glassy form.

The film forming composition suitably contains between 1 and 12% w/w of amylose-alcohol complex, between 7 and 30% w/w of the insoluble polymer and between a total of 20 and 40% of plasticiser by weight of the insoluble polymer.

The film-forming compositions are conveniently prepared by admixing an aqueous dispersion of an amylose-alcohol complex with an aqueous dispersion of the insoluble polymer and plasticiser. Typically the aqueous dispersion of the insoluble polymer is pre-plasticised by rapid, shear-mixing with an aqueous dispersion of the plasticiser. A surfactant such as Tween 80™ may be added in quantities of about 0.1% by weight of the dispersion in order to facilitate pre-plasticisation of the insoluble polymer. Alternatively the plasticiser may be mixed directly with the ethyl cellulose polymer before dispersion.

The actual concentration of the film-forming polymer used for the coating step will generally depend upon the coating methods employed. In general film forming compositions of higher concentration are required for casting methods whereas compositions of lower concentration are required for spraying methods. Compositions used for casting may comprise 22 to 80% solids by weight of the final composition whereas compositions used for spraying may comprise between 15 and 25% solids by weight, preferably between 16 and 22% w/w.

The aqueous dispersion of the amylose-alcohol complex is preferably a dispersion of an amylose-butanol complex. The concentration of the amylose-butanol complex in the dispersion may be in the range of 3 to 12% by weight of the final dispersion, preferably between 4 and 8% by weight, more preferably between 5 and 7% w/w and especially 6% w/w.

The concentration of the aqueous dispersion of the insoluble polymer may be in the range 15 to 30% by weight of the final dispersion, preferably 17 to 28%, more preferably 20 to 25% w/w and especially 25% w/w. Dispersions having concentrations outside these ranges may be used. It is preferred to use the commercially available ethyl cellulose dispersions Surelease® and Aquacoat® in the method of the present invention.

The relative proportions in which the components of the film-forming composition are mixed will depend upon the desired ratio of insoluble polymer to amylose in the final film. In general it is to be understood that the ratio of insoluble polymer to amylose in the film-forming composition is taken to be the same as that in the final film or coat formed. It is preferred that the ratio of insoluble polymer to amylose is in the range 1:1 to 7:1, preferably in the range 1:1 to 5:1 and especially in the range 3:2 to 2:1. The use of film-forming compositions having an insoluble polymer to amylose ratio outside this range, for example, 10:1 may be envisaged in certain circumstances. Particularly good results have been achieved using film-forming compositions having an insoluble polymer to amylose ratio of 5:2 and 3:2 respectively.

It is preferred that the concentration of amylose in the film-forming compositions used in the present invention is sufficient such that the amylose is in the glassy form in the films formed.

In its glassy state the structure of the polymer is generally rigid; regions of increased polymer chain movement and polymer elasticity are found in the rubbery state. Amylose exists in its glassy state below the glass transition temperature (Tg). Rising through this temperature, there is a sharp increase in the heat capacity of the amylose of 0.5±0.15 $Jg^{-1}K^{-1}$ (joules per gram per degree Kelvin). This heat capacity increment allows the Tg to be identified and can be measured by differential scanning calorimetry. Examples of procedures for obtaining Tg values and earlier literature references to such procedures are given in Orford et al, Int. J. Biol. Macromol. 1989, 11, 91.

The particular Tg of amylose in a given film or coat formed from the film forming composition of the present invention depends upon its purity and other properties. Thus, for example, the theoretical Tg for pure, dry amylose may be predicted to be 210° C. but the presence of water depresses this figure: with 10% w/w of water the Tg is 80° C. and at 20% w/w of water it is 7° C. It has been found that $\alpha$-amylolytic enzymes do not readily degrade glassy amylose and this effect is still apparent at up to 20° C. above the Tg. Such materials have been found to be sufficiently insoluble in aqueous media over the pH range 1–9 at 37° C. to be resistant to degradation in the stomach or intestine. They are, however, degraded by the enzymes produced by the faecal micro-organisms present in the colon. As indicated, the ability of glassy amylose to provide the required delayed release characteristics is not lost immediately the glassy amylose passes through the Tg and amylose which has been produced in the glassy condition at temperatures less than the Tg may therefore then be utilised at the Tg or at temperatures slightly higher than the Tg as well as at temperatures less than the Tg, whilst still retaining its glassy properties. However, the glassy amylose preferably used in the present invention has a Tg of no more than 20° C. below the temperature at which use of the composition is envisaged i.e. at body temperature of 37° C. Thus the Tg of the amylose will in the films or coats formed conveniently be 17° C. or higher and is preferably at least 30° C. or, more preferably at least about 40° C. The Tg can be predetermined by controlling the amount of water in it. This can be achieved by varying the concentration of the amylose solution, which is cooled or sprayed, and by drying the resulting gel.

The ultimate test of the suitability of a particular sample of amylose under any given conditions is its ability to resist hydrolytic degradation under aqueous conditions, particularly at a pH of 1–9 and a temperature of 37° C., and conveniently also to resist enzymatic degradation in the presence of the digestive enzymes such as normally occur in the stomach and the small intestine, but to undergo enzymatic degradation in the presence of amylose-cleaving enzymes such as are provided by the microbial flora normally present in the large intestine.

It is preferred therefore that the amylose in the film or coat formed is substantially free, i.e. contains no more than 20% by weight and preferably no more than 10% or 5% by weight, of any material which is susceptible to digestion in the stomach or small intestine. In particular the glassy amylose preferably contains no more than 10% or 5% by weight of amylopectin, for example 1 or 2% or less, and conveniently also of any material containing glucoside linkages of the type found in amylopectin. It will be appreciated that the presence of other materials in admixture with the amylose will detract from the selective nature of the degradation of this material as between the stomach and small intestine and the large intestine.

A convenient test for the purity of the amylose in the film or coat formed is provided by its iodine binding ability in a standard assay procedure such as is described by Banks et al, Starke, 1971, 23, 118. Thus pure, underivatised amylose binds with iodine to a level of about 19.5% w/w (i.e. 19.5±0.5% w/w) whereas the other main starch polysaccharide, amylopectin, binds less than 2.0% w/w and derivatisation of the amylose will also reduce this binding ability. Conveniently therefore the amylose used in the present invention binds with iodine to a level of 15.0%±0.5% w/w, or above, preferably to a level of 18.0%±0.5% w/w or above, and particularly to a level of 19.5±0.5% w/w.

It is preferred that the molecular weight of the amylose used in the invention is at least 20000 g/mol (daltons) with weights in the range of 100000 to 500000 g/mol being especially preferred. It will be appreciated that the weight of amylose used in the coating composition will depend upon the particular requirements and circumstances and may dictate that amylose having a molecular weight either below or above those weight ranges herein above described may also be advantageously used.

The release characteristics of a dosage form formed from the method of the present invention may be controlled by variations in the nature of the film-forming composition and coating conditions. The release of an active material from a dosage form has been found to be dependent on, without limitation, the ratio of insoluble polymer to amylose in the coat, the amount of plasticiser used, the coat thickness employed and the solubility characteristics of the active material coated.

Compositions having a high insoluble polymer to amylose ratio, such as 10:1 or 7:1 have been found to give rise to films that significantly retard release of an active material. Compositions having a low insoluble polymer to amylose ratio of 1:1 have been found to form films that are less able to retard drug (active material) release to a significant extent. Compositions having an insoluble polymer to amylose ratio of between 5:2 and 3:2 have been found to form films that are able to substantially inhibit release of drug during the period in which the dosage form is in the stomach and small intestine, but allow dissolution or release of the drug subsequently.

The rate of release of an active material from a dosage form has been found to be dependent on the thickness of the coat or film-formed with the dissolution of active material being retarded to a greater extent with a thicker film. The thickness of the film is suitably chosen to prevent the release of the active material during the passage of the dosage form through the stomach and small intestine but to allow release thereof in the colon. In practice the chosen thickness of the coat will also depend upon the nature of the film-forming composition as well as the solubility of the active material that it is desired to coat. It is preferred to use thicker coats when the ratio of insoluble polymer to amylose is low or when the solubility of the active material is high. Thinner coats are preferred when the ratio of insoluble polymer to amylose is high or the solubility of the active material is low.

The plasticiser used in the film-forming composition is preferably hydrophobic in nature, although hydrophilic plasticisers may be used where they do not inhibit the film forming properties of the composition. The amount of plasticiser added to the dispersion of the insoluble polymer will depend upon whether or not the insoluble polymer has been pre-plasticised, that is to say whether or not a plasticiser has been added to the insoluble polymer prior to the formation of the dispersion. If the insoluble polymer has not been pre-plasticised, between 20 and 40% of plasticiser by weight of insoluble polymer may be added to the dispersion of insoluble polymer prior to its incorporation in the film forming composition, preferably between 24 and 36% by weight. If the insoluble polymer has been pre-plasticised, between 5 and 15% of plasticiser by weight of pre-plasticised insoluble polymer may be added to the dispersion of insoluble polymer prior to its incorporation in the film forming composition. The actual amount of additional plasticiser added to a pre-plasticised insoluble polymer will depend upon the extent to which the insoluble polymer has been pre-plasticised and it is preferred that the total amount of plasticiser present in the dispersion (amount of plasticiser present in pre-plasticised polymer+any additional plasticiser) does not exceed 40% by weight of the weight of the insoluble polymer. If inadequate plasticiser is present (less than 20%) the film is characterised by the present of fragments, is brittle and is of insufficient strength. If too much plasticiser is present (more than 40%) the film is characterised by a wrinkly appearance and the polymer is in a semi-solid state. As before, such films are of insufficient strength to withstand the mechanical forces experienced by a dosage form during this passage through the GI tract. Film-forming compositions comprising between 24 and 36% of plasticiser by weight of insoluble polymer give a smooth, clear, continuous films that are of good mechanical strength and are associated with dissolution profiles which render them suitable for use in the colonic delivery of an active material.

The amount of plasticiser present in the film has also been found to effect the dissolution profile of an active material. A high concentration of plasticiser is associated with a slower rate of release of the active material from the dosage form. It will therefore be appreciated that the amount of plasticiser included in the film-forming compositions will depend, in part, upon the relative quantities of insoluble polymer and amylose present in the film as well as the thickness of the coat formed. If the ratio of insoluble polymer to amylose is high less plasticiser is required. Less plasticiser is also required if a large coat thickness is employed.

Examples of plasticiser that may be used in the film forming compositions used in the method of the present invention include dibutyl sebacate, triethyl citrate, triacetin, acetyl tributyl citrate, hydrogenated coconut oil and tributyl citrate. If the insoluble polymer of choice is Surelease® the preferred plasticisers are dibutyl sebacate, acetyl tributyl citrate, hydrogenated coconut oil and tributyl citrate, especially dibutyl sebacate. If Aquacoat is used as the insoluble polymer dispersion the preferred plasticisers are dibutyl sebacate, triethyl citrate, triacetin, acetyl tributyl citrate and tributyl citrate. Dibutyl sebacate and tributyl citrate are especially preferred when Aquacoat® is used.

It will be appreciated that the method according to the first aspect of the invention is particularly suitable for the preparation of dosage forms comprising a thermolabile active ingredient. A second aspect of the invention, therefore, provides a dosage form comprising a thermolabile active ingredient, the dosage form being coated in accordance with the method according to the first aspect of the invention. The active ingredient may be present in admixture with any suitable carrier or excipient or any other active ingredient. By the term "thermolabile" it is to be understood that the active materials is unstable and has a tendency to degrade at temperatures greater than 60° C., preferably 50° C. and especially 40° C.

It is believed that the film-forming compositions comprising a hydrophobic plasticiser used in the method according to the first aspect of the invention are new per se. A third aspect of the present invention provides a composition comprising an aqueous dispersion of an amylose-alcohol dispersion, an insoluble film forming polymer and a hydrophobic plasticiser. The nature and relative quantities of the components of the composition have been discussed herein above.

As indicated previously, the dosage forms prepared in accordance with the first aspect of the invention find particular application for use in therapy, particularly for use in diseases of the colon and conditions, the therapeutic management of which is best effected via the colon. The present invention therefore provides the use of a dosage form according to the second aspect of the invention for use in therapy.

The present invention also provides a method of therapy, said method comprising the administration to a patent of a dosage form prepared in accordance with the first aspect of the invention.

The invention will now be described with reference to the following, non-limiting, examples. Variations of these examples falling within the scope of the invention will be apparent to a person skilled in the art.

EXAMPLE 1

Investigations of Ethyl Cellulose Films Formed at Temperatures Below 37° C.

(a) The Methods Used to Evaluate the Influence of Plasticiser Quantity, Incorporation Technique and Type on the, Minimum Film Forming Temperature (MFFT) of Ethyl Cellulose Dispersions Surelease® EA7100 and Aquacoat® ECD30

Two different methods were used to evaluate the influence of plasticiser type, quantity and incorporation technique on the MFFT on Surelease® EA7100 and Aquacoat® ECD30. The minimum film-forming temperature (MFFT) is the lowest temperature at which the film-forming composition solidifies to form a film.

(i) Visual Evaluation

The first was by pouring the dispersions onto glass petri dishes. These dispersions were dried at ambient temperature (15–25° C.) in Class 2 cleanroom environment and inspected visually. All visual observations were graded using a numerical grading system, shown in Table 1. They referred to the plasticisation level needed to form films at 20±5° C. The same numerical grading system was used to evaluate the mixed films of examples 2 to 4.

TABLE 1

The numerical grading system used to evaluate the success of plasticisation for formulations dried at 20 ± 5° C.

| Number Grading | Indication | Observations and Comments |
|---|---|---|
| 1 | Over-plasticisation | A wrinkly, continuous film. The polymer is in a semi-solid state. Partial solidification gives rise to a wrinkled-surface appearance |
| 2 | Optimum plasticisation | A smooth, clear, continuous film |
| 3 | Under-plasticisation | A smooth, clear film with fine fissures. Slight increase in plasticisation level is needed. |
| 4 | Under-plasticisation | Clear, film fragments. Large increase in plasticisation level is needed. |
| 5 | No plasticisation | Opaque, powder compacts. Plasticisation incorporation technique has failed completely. |

(ii) Evaluation Using MFFT Bar

The second method determined the specific MFFT for each formulation. A MFFT bar was used. The hot water bath on one end of the MFFT bar was set at 46±1° C. and the cold water bath on the other end was set at 3±1° C. This created a temperature gradient of 32.5±1.0° C. to 12±1.0° C. across the spreading surface. The temperature gradient across the MFFT bar was allowed to equilibrate for at least two hours prior to use. The temperatures were measured at the beginning and at the end of each experiment using a Jenway 3070 digital-display thermometer. The apparatus was levelled using the adjustable support and a spirit level. The plasticised dispersion formulations were spread across the surface. Once spread, the film was allowed to form at room humidity. After the film had dried, the lowest temperature on the bar at which the film was still continuous was taken as the MFFT. If the film became discontinuous in between two temperature sampling points then the higher of the two sampled temperatures was taken to be the MFFT. All experiments were duplicated. The reported MFFT was an average of the four temperatures taken at the beginning and at the end of each duplicate experiment.

(b) Investigations of the Influence of Plasticiser Quantity Incorporation Technique and Type on the MFFT on Surelease® EA 7100 and Aquacoat® ECD30

The quantity of plasticiser added was expressed as % w/w of the solids content of its ethyl cellulose dispersion. In this study, this percentage was defined as:

$$\%\text{w/w of plasticiser} = \frac{\text{(the content of the added plasticiser)}}{\left(\begin{array}{c}\text{the solid contents of the ethyl} \\ \text{cellulose dispersions}\end{array}\right)} \times 100$$

Surelease® EA7100 was taken as a 25% w/w solids dispersion; Aquacoat® ECD30 was taken as a 30% w/w solids dispersion. Based on this definition, the % w/w of plasticiser in all Surelease® formulations was only reflective of the added plasticiser, not the true amount present. Even without additional plasticiser, Surelease® already contained 24% w/w of dibutyl sebacate plasticiser. Therefore, the quantities of plasticiser added to the Surelease® dispersions were often much less than the quantities added to the Aquacoat® dispersions.

Four different plasticiser incorporation techniques were evaluated.

The first was by direct mixing of a plasticiser with an aqueous ethyl cellulose dispersion using a magnetic stirrer. The plasticiser was mixed for half-an-hour, 24 hours and 72 hours. Thirty percent w/w of dibutyl sebacate was added to Aquacoat® and 6% w/w of dibutyl sebacate was added to Surelease®. The plasticised dispersions were cast in duplicate onto glass petri dishes.

The second technique involved the addition of Tween 80, a surfactant. The plasticiser and Tween 80™ were mixed with a magnetic stirrer for 5 minutes. Then, the ethyl cellulose dispersion was added and stirred for a further 30 minutes with a magnetic stirrer. After 30 minutes, water was added. The final formulation was then passed through a hand-operated homogeniser. The final formulation was cast in duplicate onto glass petri dishes and dried under the conditions mentioned above. Compositions comprising 1% Tween 80™ and between 10 and 50% of added plasticiser were investigated. Aquacoat® ECD30 was plasticised with dibutyl sebacate, triethyl citrate and triacetin In the third technique, the required amount of plasticiser, Tween 80™ and the pseudolatex were mixed with a high speed Silverson homogeniser mixer for 3 minutes. The additional plasticiser content of compositions comprising Surelease® has between 0 and 12% by weight of the ethyl cellulose solids. For compositions comprising Aquacoat®, plasticiser contents of between 18 and 30% by weight of the ethyl cellulose solids were investigated. In all cases Tween 80™ was present in an amount of 0.01% by weight of the dispersion. The formulations were left overnight in sealed containers. Any formulations that remained foamy after overnight storage were not investigated further. Otherwise, the formulations were evaluated on the MFFT apparatus. The plasticisers used were dibutyl sebacate, triethyl citrate, triacetin, acetyl tributyl citrate, tributyl citrate, polypropylene glycol, glycerol and polyethylene glycol 400.

In the final technique, Tween 80, the plasticiser and water were premixed into a crude emulsion prior to addition to ethyl cellulose coating dispersions. A plasticiser emulsion was formed by mixing parts of plasticiser and water with 0.1% of Tween 80™ using a Silverson homogeniser mixer. The freshly mixed plasticiser emulsion was then added to the ethyl cellulose coating dispersion by magnetic stirring for 30 minutes. Preliminary studies suggested that 30 minutes mixing time was sufficient. Only Aquacoat® ECD30 formulations were investigated. Aquacoat® ECD30 was plasticised with dibutyl sebacate, triethyl citrate, triacetin, acetyl tributyl citrate, tributyl citrate, polypropylene glycol, glycerol and polyethylene glycol 400. The basic formulations comprise between 18 and 36% of plasticiser by weight of solids in the dispersion and 0.1% w/w Tween 80.

Results

Inconsistent results were obtained from formulations formed by admixing the ethyl cellulose dispersion with a plasticiser using a magnetic stirrer. The properties of the formulations were improved by mixing the components at an increased speed. This was achieved by replacing the magnetic stirrer with a high-shear mixer. The high shearing actions of the mixer allowed more intimate mixing between the plasticiser and the polymer. The high input of energy also increases the rate of solvation of the plasticiser for the present investigation and a Silverson mixer was used instead. The mixing action drew a lot of air into the dispersions. The final mixtures were left overnight to allow the air bubbles to disperse.

The plasticised ethyl cellulose films obtained using a high-shear mixing procedure were reproducible. No oily patches or tiny gas bubble structures were seen suggesting that good plasticiser permanence had been achieved. The MFFT was lowered by hydrophobic plasticisers only e.g. dibutyl sebacate, acetyl tributyl citrate and tributyl citrate; the hydrophilic plasticisers had little to no effect on the MFFT of Surelease®. This technique was successful in incorporating plasticisers into Surelease®. All hydrophobic plasticisers tested, dibutyl sebacate, tributyl citrate and acetyl tributyl citrate, were the plasticisers which had been shown to be effective in lowering the MFFT of Surelease®.

The fourth plasticiser incorporation technique was developed for Aquacoat® formulations. This involved forming a plasticiser emulsion containing 50% of water prior to addition to the dispersion. As the presence of additional water would dilute the dispersion and increase spray coating time this technique was only used when the previous technique was not suitable.

Using this technique, the Aquacoat® films formed were found to be reproducible and good plasticiser permanence was achieved. Contrary to previous findings, the MFFT of Aquacoat® was affected by selected hydrophobic and hydrophilic plasticisers. The success of hydrophilic plasticisers e.g. triethyl citrate and triacetin, in lowering the MFFT could be due to the influence of the other excipients such as stabilisers and antifoaming agents present in Aquacoat®.

When the MFFT of plasticised Surelease® formulations were compared with the MFFT of plasticised Aquacoat® formulations, some common features were seen. In both cases, dibutyl sebacate, acetyl tributyl citrate and tributyl citrate were successful in lowering the MFFT. On the other hand, glycerol, polyethylene glycol 400 and polypropylene glycol were unsuccessful. The lowering of the MFFT of Surelease® by dibutyl sebacate, acetyl tributyl citrate and tributyl citrate and the lowering of the MFFT of Aquacoat® by dibutyl sebacate, acetyl tributyl citrate, tributyl citrate, triethyl citrate and triacetin all appeared to be directly proportional to the concentration of the added plasticiser.

EXAMPLE 2

Investigations of the Combined Amylose/ethylene Films Formed at Temperatures Below 37° C.

The amylose-butanol dispersions used in the preparation of the film-forming compositions of the present invention were prepared from pea starch powder. Amylose fractions were isolated by sequential leaching of the pea starch powder under an atmosphere of nitrogen. Swollen gelatinised starch granules (mainly amylopectin) were removed by mild centrifugation (2000G) and filtration through a glass sinter filter (porosity 2). Amylose was precipitated as its amylose-butanol complex by the addition of butan-1-ol to the filtrate. After storage at +1° C. for 24 hours, the butan-1-ol complex was collected by centrifugation. This complex was dispersed in water prior to incorporation in the film-forming composition.

(a) Investigations on the MFFT of the Polymeric Formulations

Ethyl cellulose dispersion was first plasticised with the required quantity of plasticiser. Aquacoat® and Surelease® were plasticised using a different plasticisation techniques as indicated in Example 1. The plasticised ethyl cellulose dispersion was then mixed with the aqueous amylose alcohol dispersion by stirring for 5 minutes with a magnetic stirrer. In all of the following formulations, the ratios of ethyl cellulose to amylose are by weight of the ethyl cellulose and amylose solids present in the dispersions. The final dispersion mixtures were then spread onto the MFFT bar surface.

Various temperature gradients were set across the MFFT bar surface. Such variations were deemed necessary to avoid the MFFT being too close to either end of the MFFT bar. Only formulations containing dibutyl sebacate plasticiser were investigated. All experiments were done in duplicate. Formulations having an ethyl cellulose (either Aquacoat® or Surelease®) to amylose weight ratio of 1:0, 7:1, 5:1 and 3:1 were investigated. When Aquacoat® was used as the ethyl cellulose dispersion, the effect of adding 24, 30 and 36% of plasticiser per weight of ethyl cellulose solids was investigated. When Surelease® was used as the ethyl cellulose dispersion, the effect of adding 0, 4, 8 and 12% of plasticiser per weight of ethyl cellulose solids was investigated. As indicated in Example 1, commercially available Surelease® already contains 24% of dibutyl sebacate plasticiser by weight of the ethyl cellulose solids.

(b) Casting of the Mixed Polymer Free Films

The mixed polymeric formulations were prepared as described in (a) above. They were poured onto PTFE petri dishes and dried at 35° C. in a fan-assisted oven (Pickstone oven, serial no. 16254). The dried films were then stored for at least 24 hours in a temperature and humidity-controlled environment prior to further testing. Saturated potassium carbonate salt solution was used to maintain 44% RH within the desiccator stored at 20° C.

The mixed polymer formulations formed films at the drying temperature of 35° C. However some of the films formed may be too brittle or too soft to be handled as free films. Films containing Surelease®/amylose+4% w/w dibutyl sebacate (DBS) AND Aquacoat®/amylose+36% DBS, at various polymer ratios were considered the easiest to handle as free films. These formulations were used for further film studies.

Results (a) Investigations of the Minimum Film Forming Temperature (MFFT) of the Polymeric Formulations.

The MFFTs of the polymeric formulations are shown in Table 2.

TABLE 2

The minimum film forming temperatures (MFFT) of the mixed polymeric formulations as measured by MFFT bar

| Product name | Ethyl cellulose: amylose | plasticiser (% w/w) | MFFT (± 0.1° C.) | | |
|---|---|---|---|---|---|
| | | | $T_1$ | $T_2$ | $T_{av}$ |
| Aquacoat ® | 3:1 | 24 | 16.9 | 22.4 | 19.7 |
| Aquacoat ® | 5:1 | 24 | 20.3 | 24.2 | 22.3 |
| Aquacoat ® | 7:1 | 24 | 22.1 | 26.1 | 24.1 |
| Aquacoat ® | 1:0 | 24 | 23.9 | 26.1 | 25.0 |
| Aquacoat ® | 3:1 | 30 | 12.9 | 12.3 | 12.6 |
| Aquacoat ® | 5:1 | 30 | 14.0 | 12.3 | 13.2 |
| Aquacoat ® | 7:1 | 30 | 14.0 | 14.8 | 14.4 |
| Aquacoat ® | 1:0 | 30 | 17.6 | 19.3 | 18.5 |
| Aquacoat ® | 3:1 | 36 | <7.4 | <7.6 | <7.5 |
| Aquacoat ® | 5:1 | 36 | <7.4 | 7.6 | 7.5 |
| Aquacoat ® | 7:1 | 36 | 9.1 | 10.3 | 9.7 |
| Aquacoat ® | 1:0 | 36 | 9.1 | 10.3 | 9.7 |
| Surelease ® | 3:1 | 0 | <12.0 | 13.7 | 12.9 |
| Surelease ® | 5:1 | 0 | 24.7 | 20.7 | 22.7 |
| Surelease ® | 7:1 | 0 | 27.7 | 26.3 | 27.0 |
| Surelease ® | 1:0 | 0 | >31.8 | >32.3 | >32.1 |
| Surelease ® | 3:1 | 4 | <12.1 | <12.0 | <12.1 |
| Surelease ® | 5:1 | 4 | <12.1 | <12.0 | <12.1 |
| Surelease ® | 7:1 | 4 | <12.1 | <12.0 | <12.1 |
| Surelease ® | 1:0 | 4 | 24.2 | 22.6 | 23.6 |
| Surelease ® | 3:1 | 8 | <9.5 | <9.5 | <9.5 |
| Surelease ® | 5:1 | 8 | <9.5 | <9.5 | <9.5 |
| Surelease ® | 7:1 | 8 | <9.5 | <9.5 | <9.5 |
| Surelease ® | 1:0 | 8 | 15.3 | 15.6 | 15.5 |
| Surelease ® | 3:1 | 12 | <8.0 | <8.0 | <8.0 |
| Surelease ® | 5:1 | 12 | <8.0 | <8.0 | <8.0 |
| Surelease ® | 7:1 | 12 | <8.0 | <8.0 | <8.0 |
| Surelease ® | 1:0 | 12 | 13.9 | 14.0 | 14.0 |
| Amylose | 0:1 | 0 | <7.5 | <7.5 | <7.5 |

$T_1$ and $T_2$ = The average of temperatures measured at the beginning and at the end of each experiment.
$T_{av}$ = The average of temperatures $T_1$ and $T_2$ for the formulation From the results it can be seen that the addition of an aqueous dispersion of an amylose-butanol complex to an ethyl cellulose dispersion lowers the MFFT of the final mixed polymer dispersion relative to that of the ethyl cellulose dispersion per se. All the mixed formulations were shown to have MFFTs of at least 10° C. below 37° C. which means that all the compositions tested were potentially suitable for spray-coating onto solid dosage forms at 37° C. The extent by which the MFFT was lowered was found to be dependent upon the amount of amylose present in the sample. Compositions having a higher amount of amylose were found to have lower MFFTs than compositions having a great amount of insoluble polymer. In addition it also appears that by increasing the amount of plasticiser present in the composition the MFFTs are also lowered.

EXAMPLE 3

Investigations of the Digestion of the Mixed Polymeric Films in Simulated Colonic Media Cast and sprayed mixed polymeric free films comprising ethyl cellulose, amylose and a plasticiser were tested for digestion in the in vitro fermentation model. The cast films were formed by the method described in Example 2 (b) above. The thickness of the films were kept as uniform as possible by casting mixed polymeric dispersions equivalent to predetermined dried solid weight in each case.

Sprayed films were formed by spraying the dispersion formulations repeatedly onto a large piece of tin foil in a temperature controlled chamber set at 35° C. A table fan was housed within this chamber to increase the rate of drying of the dispersion. The dispersion was sprayed using a spray gun attached to a pressurised aerosol can. Comparatively large amounts of coating dispersions were required to form very thin films due to loss on spraying. Hence, studies using sprayed films were limited.

All the films were stored for 7 days at 20° C. and 44% RH before being cut into strips of approximately (3×1) cm². The strips of films were accurately weighed using a Sartorious 2001 MP2 balance, then placed in coded nylon mesh bags. The bag size was (2×8) cm², mesh size=(1×0.4) cm². The controls were incubated in phosphate buffers, the tests were incubated in faecal slurries.

The simulated colonic media used in the investigation contained (10–15)% w/w of freshly voided human faeces and was made up using the following buffer solution.

| Materials | g/L (in double deionised water) |
|---|---|
| $K_2HPO_4$ | 1.5 |
| $KH_2PO_4$ | 1.5 |
| NaCl | 4.5 |
| $MgCl_2.6H_2O$ | 0.5 |
| $FeSO_4.7H_2O$ | 0.05 |
| $CaCl_2.2H_2O$ | 0.15 |

The buffer was boiled for at least 15 minutes to aid the dissolution of the salts as well as the removal of oxygen. This buffer solution was then cooled in a water bath to 37° C. Nitrogen was constantly bubbled into the buffer solution throughout this cooling process. Half of the buffer solution was used as control solution. The other half was inoculated with faeces. The required quantity of faeces was weighed and added to the buffer solution. Homogenisation of the faeces in the buffer was done using a stomacher machine (stomacher 3500, Colworth). The faecal slurry was filtered through a 500 μm sieve to remove any fibrous materials that was not homogenised. A 100 ml of this slurry was then filled into each test bottle. The films within the nylon-meshed bags were added and the bottles were sealed under positive nitrogen pressure using rubber stoppers and metal crimping. The bottles were then left unstirred in a 37° C. incubator.

After either 6 or 24 hours of incubation, the films within the nylon-meshed bags were retrieved. The strips of films were carefully collected, washed with distilled water and then dried between filter papers before being stored at 20° C., 44%RH for 7 days. After 7 days, the films were reweighed on a Sartorious 2001 MP2 balance. All film fragments were carefully washed and collected. Fragments as small as (0.2×0.2) cm² were retained due to adhesion onto the nylon mesh. The formulations of the mixed polymeric films tested for digestion together with the % weight of film left after digestion is shown in Table 5.

Results

Investigations of the Digestibility of the Mixed Polymeric Films

All the three films in the fermentation experiment had different weights at the onset of the experiments. To make comparisons, the digestibility of the film was expressed as the percentage of film left after digestion. The percentage weight of film left, as shown in Table 5 was calculated as follows:

% of film left=(final film weight/initial film weight)×100

Amylose films formed by spraying or casting had comparable digestibility profiles. Therefore, cast films were considered valid models for testing the digestibility of eventually spray-coated films.

The percentage of film digested and the quantity of amylose present within the mixed Surelease®/amylose film appeared to be related. As the amylose content of the film was increased, the degree of weight loss was also increased. This suggested that the digestible fraction within the film was most likely to be amylose. This was further confirmed by iodine tests. When films recovered from 24 hours of incubation in the fermentation studies were stained with iodine and viewed under light microscope, there were no regions within the Surelease®:amylose (1:1)+4% DBS film which turned dark blue indicating that the amylose fraction within the film had been digested away. This showed that the present of increased hydrophobic plasticiser within this film had not prevented the digestion of amylose.

TABLE 5

The percentages of film left after digestion in vitro fermentation testing system

| Film formulation | % Film left | | | |
|---|---|---|---|---|
| | Test | | Control | |
| [Sprayed (S) or Cast (C)] | 6 hrs | 24 hrs | 6 hrs | 24 hrs |
| Amylose (C) | 57.4 | 0.0 | 102.2 | 100.0 |
| Amylose (S) | 32.2 | 0.0 | 95.7 | 76.6 |
| Avebe* (C) | ND | ND | ND | ND |
| Surelease ®:amylose (1:1) + 4% DBS (C) | 72.7 | 51.0 | 97.8 | 94.5 |
| Surelease ®:amylose (3:1) + 4% DBS (C) | 73.6 | 70.1 | 99.2 | 98.4 |
| Surelease ®:amylose (5:1) + 4% DBS (C) | 86.5 | 81.2 | 92.3 | 105.1 |
| Surelease ®:amylose (5:1) + 4% DBS (S) | 99.5 | 91.7 | 100.0 | 100.0 |
| Surelease ®:Avebe* (3:1) + 4% DBS (C) | 87.2 | 83.1 | 92.5 | 90.4 |
| Aquacoat:amylose (1:1) + 36% DBS (C) | ND | ND | ND | ND |
| Aquacoat:amylose (3:1) + 36% DBS (C) | ND | ND | ND | ND |
| Aquacoat:amylose (5:1) + 36% DBS (C) | ND | ND | ND | ND |
| Aquacoat:amylose (5:1) + 36% DBS (S) | 94.9 | 88.2 | 95.7 | 94.6 |

*Avebe = amylose-butanol complex from Avebe, Netherlands
ND = Not done

No continuous Avebe films were produced, only clear film fragments.

Although continuous Aquacoat® mixed films were produced they were too brittle to be removed from the PTFE plates. The continuous films cracked easily and no sufficiently large pieces of films could be obtained for testing.

When iodine was used to stain the Surelease®:amylose (3:1) and (5:1) films which had undergone 24 hours of digestion however, some regions of the film still turned dark blue with iodine although such regions seemed less compared to those which had not undergone digestion. This would indicate that although amylose was still digestible when mixed with plasticised ethyl cellulose, its rate of digestion was different. This change in the rate of digestion could be due to one or more of the following reasons:

The increased presence of ethyl cellulose could result in amylose being less accessible to enzymatic attack because the amylose domains were no longer continuous through the cross-section of the film. The inaccessibility would be greatest when the ratio of ethyl cellulose to amylose within the film was highest.

The presence of plasticiser could also have affected the rate of digestion of amylose. Most bacterial enzymes cannot digest fats and oils and would not naturally be attracted to a non-substrate surfaces. Since the presence of dibutyl sebacate was directly proportional to the presence of ethyl cellulose, the rate of digestion of amylose would decrease with the increasing ethyl cellulose to amylose ratio.

Thirdly, the rate of digestion of amylose could be affected by inhibition of swelling of amylose by ethyl cellulose. The digestion of other polymers had been shown to be affected when their maximum swelling abilities were reduced (Rubinstein and Gliko-Kabir, 1995)

The other important observation during this study was the inability of the amylose-butanol complex dispersion supplied by Avebe to form continuous films. The Avebe amylose was prepared by the hydrolysis of amylopectin derived from potato starch. This lack of continuous film structure was attributed to its low molecular weight fractions. There were more low molecular weight fractions in the amylose from Avebe than in the other amylose used in this study. This indicates that there is a direct correlation between the molecular weight of a polymer and its film-forming properties. Better film-forming properties could be found in higher molecular weight polymers.

The digestion of amylose within an Aquacoat®/amylose mixed film could only be evaluated using sprayed films. Sprayed films, unlike cast films, showed greater experimentation errors. They tend to peel from their tin foil backing showing loss even in control experiments. In addition, the tin foil backing also reduced the rates of digestion by allowing digestion from only one side of the film. Nevertheless, the loss of film was greater in Aquacoat®/amylose films incubated in the faecal slurries compared with those incubated in the phosphate buffer. This suggested that amylose within a highly plasticised Aquacoat® film was digestible. The digestion rate was also comparable to Surelease®:amylose (5:1)+4% DBS sprayed film.

In conclusion, the amylose fractions within mixed films formed at temperature below 37° C. were digestible. However, the rate of digestion of this amylose fraction decreased when the ratio of ethyl cellulose to amylose increased. This suggests that coats or films formed from these mixed compositions are suitable for delivery of an active ingredient to the colon.

EXAMPLE 4

Dissolution Tests

These were carried out using pellets form from 5-Aminosalicyclic Acid (5-ASA) (30%) glucose (30%) and Avicel® (40%). The pellets were referred to as AGI pellets.

5-ASA was used as it finds application in the treatment of conditions such as irritable bowel syndrome (IBS). The dissolution profile of a series of coated and uncoated pellets in phosphate buffer, simulated gastric and simulated colonic solutions respectively was determined.

The pellets were spray-coated with a series of coating formulations similar to those specified to investigate the influence of various formulation variables. The Surelease®/amylose system was studied using a two way analysis of variance. The two variables were coat thickness and the Surelease® to amylose ratio. No additional plasticiser was incorporated.

The Aquacoat®/amylose system was studied using a three way analysis of variance. The three variables were coat thickness, Aquacoat® to amylose ratio and plasticiser quantity.

The following ingredients were used for the preparation of the coating formulations:

(a) Aqueous dispersion of amylose-butanol complex made and concentrated to 6% w/w
(b) Surelease® EA7100 from Colorcon, USA, Batch No. 600041-1.
(c) Aquacoat® ECD30 from FMC Corporation, USA, Batch No. J3202
(d) Tween 80, technical grade, from Merck, UK Batch No. 3139220

The coated pellets were tested in simulated gastric and small intestinal conditions using media made up of:

(a) 5N Hydrochloric acid, AnalaR grade, Merck, UK, Batch No. 50065821
(b) Potassium dihydrogen orthophosphate, AnalaR grade, Merck, UK Batch No. A890225
(c) Sodium hydroxide pellets, AnalaR grade, Merck, UK Batch No. 050594H225S
(d) Pepsin from Sigma, UK Potency 1:2500 Batch No. 45H0867
(e) Pancreatin from Sigma UK Potency equivalent to USP specification Batch No. 100H0124.
(f) Citric acid, general purpose grade, Merck, UK Batch No. 3863580M
(g) Disodium phosphate, general purpose grade, Merck, UK Batch No. 5029200M The coated pellets were test in simulated colonic conditions using media made up according to the formula mentioned in Example 3 with the following chemicals from Merck, UK:

(a) Dipotassium hydrogen phosphate, AnalaR grade, Batch No. 302A604476
(b) Potassium dihydrogen phosphate, AnalaR grade, Batch No. A890225551
(c) Sodium Chloride, GPR grade, Batch No. L20603432
(d) Magnesium chloride, $MgCl_2 \cdot 6H_2O$. GPR grade, Batch No. TA576032
(e) Ferrous sulphate, $FeSO_4 \cdot 7H_2O$, GPR grade, Batch No. A843740522
(f) Calcium Chloride, $CaCl_2 \cdot 2H_2O$, GPR grade, Batch No. TA69532 445

(a) Preparation of Aqueous Coating Formulations

The ethyl cellulose coating dispersions were plasticised prior to mixing with amylose.

Surelease® was used with or without additional plasticiser. Mien Surelease® was mixed with additional plasticiser, the required quantity of dibutyl sebacate (DBS) was added to Surelease® and mixed with high shear mixing using a Silverson mixer for 3 minutes. The mixture was covered and left overnight to remove the foam formed during mixing. The required quantity of plasticised Surelease® dispersion was then mixed at room temperature, with an amylose-butanol complex dispersion using a low-speed magnetic stirrer. Stirring was maintained throughout coating.

Aquacoat® could not be plasticised directly with the required quantity of plasticiser, instead it was plasticised with a plasticiser dispersion. The DBS plasticiser was made up using 50% DBS, 0.1% Tween 80™ and 49.9% water (R ohm Pharma, 1993). The resulting mixture was mixed with Silverson mixture to give a crude emulsion. This had to be freshly prepared.

Aquacoat® was therefore mixed with the plasticiser dispersion by magnetic stirring for 30 minutes prior to addition of amylose-butanol complex dispersion. Stirring was maintained throughout coating. The process of plasticisation of Aquacoat® was carried out at room temperature.

All calculations relating to the proportion of each component present in coating formulations prepared were based on dry solids weight. All the percentages of DBS in the experiments were expressed as percentages of ethyl cellulose dry polymer weight and not the total polymer weight of the system. This approach was adopted as DBS was an ethyl cellulose plasticiser, which was incorporated prior to addition of amylose. Examples of calculations from each formulation systems are as follows:

| Coating materials (% w/w) | Polymer solids (g) | Dispersions (g) |
|---|---|---|
| Surelease ®:amylose (5:1) + 4% DBS | | |
| Surelease ® (25% w/w) | 5.0 | 20.0 |
| Amylose (6% w/w) | 1.0 | 16.7 |
| DBS | 0.2 | 0.2 |
| Aquacoat:amylose (5:1) + 36% DBS | | |
| Aquacoat ® (30% w/w) | 5.0 | 16.7 |
| Amylose (6% w/w) | 1.0 | 16.7 |
| DBS (50% w/w) | 1.8 | 3.6 |

The 7:1 and 3:1 ethyl cellulose-amylose formulations were prepared in a similar way.

(b) Fluid Bed Coating

The pellets were coating in a bottom-sprayed fluidised bed under the following conditions:

| | |
|---|---|
| Batch Size | 40 g |
| Coat Weight | 4 g |
| Inlet Temperature | 36° C. |
| Outlet Temperature | 32° C. |
| Atomising Air Pressure | 0.1 bar |
| Spray Rate | 0.6–0.7 ml/min |
| Fluidisation Air | 13 Units |
| Drying Time | 30 minutes |

The thickness of the coat was expressed in terms of the theoretical weight gain, TWG, defined as:

$$TWG = \frac{\text{Coat weight}}{\text{weight of the pellets} + \text{coat weight}} \times 100$$

The TWG was 9.1% for pellets tested under these conditions. They were stored at 45% relative humidity for at least 48 hours before dissolution testing.

(c) In vitro Dissolution Studies

The coated pellets were tested using the paddle-stirred dissolution testing apparatus, PharmaTest Mode PTWS (Apparatebau, Germany). The quantity of pellets equivalent to 500 mg of uncoated pellets were placed in 900 ml of dissolution medium maintained at 37° C. The medium was stirred continuously at 100 rpm. For the first 3 hours 0.1N HCl (pH 1.5) was used as dissolution medium. This was followed by 9 hours in phosphate buffer pH 7.2. At specific intervals, 3 ml samples were withdrawn by means of an automated sampler (PharmaTest, Apparatebau, Type PTFC1, Germany). The samples were then measured for absorbence using a UV-Vis spectrophotometer (Perkin-Elmer 554) at 302 nm for 0.1N HCl and 332 nm for phosphate buffer.

The in vitro release of 5-ASA from the most acceptable coating formulation was further evaluated under the simulated gastrointestinal conditions. 900 ml of freshly prepared simulated gastric fluid (0.1N HCl containing 0.32% w/v pepsin) was used as the dissolution media for the first three hours and then replaced with 900 ml of freshly prepared simulated intestinal fluid (0.2M phosphate buffer containing 1% w/w pancreatin) for an additional nine hours. The samples were centrifuged and filtered through 0.2 μm filters prior to measurement for absorbence.

5-ASA had previously been shown to absorb linearly in both the acid and phosphate buffers. The concentration of 5-ASA released from the coated pellets was calculated from the calibration surveys.

Release of Glucose

The in vitro release of glucose was evaluated using the mixed acid/phosphate buffer and the procedure described for 5-ASA above. The glucose concentration was measured using a Glucose-GOD PERID® diagnostic kit (Boehringer Manheim).

(d) In Vitro Fermentation Studies Using Simulated Colonic Media

The fermentation test system was a batch culture test system which had previously been used to test digestibility of free films. The system was tested to compare the release performance of uncoated pellets in the shaken and unshaken testing conditions. The volume of the fermentation medium and the quantity of pellets were also varied to investigate the optimum testing condition for 5-ASA within this medium. All experiments were done in duplicate.

Prior to the study of 5-ASA release from coated pellets in the colon, a study was done to investigate the stability of 5-ASA in faecal slurry. In this study, known amounts of 5-ASA powder was added to 100 ml each of faecal slurry and phosphate buffer in anaerobically sealed bottles which were shaken under the same conditions as the testing procedure mentioned below. Samples were taken periodically and were treated in the same manner as the test samples. The content of 5-ASA in these samples was measured using high performance liquid chromatography.

Prior to testing a known quantity of the pellets were soaked in 100 ml of 0.1N HCl for a maximum of 30 minutes before being transferred to a simulated colonic medium in anaerobically sealed bottles. The bottles were sealed under a positive pressure of nitrogen and were laid horizontally in an incubator shaker at 37° C. with a rotor arm speed of 100 rpm throughout the experiment. 2.0 ml samples were withdrawn from the bottles at specific times. These samples were centrifuged for 5 minutes at 1300 rpm. The clear supernatant liquid was removed and centrifuged for a second time at 13000 rpm for 5 minutes. Finally the supernatant was filtered through 0.2 μm filter and analysed using HPLC.

Figure 2:
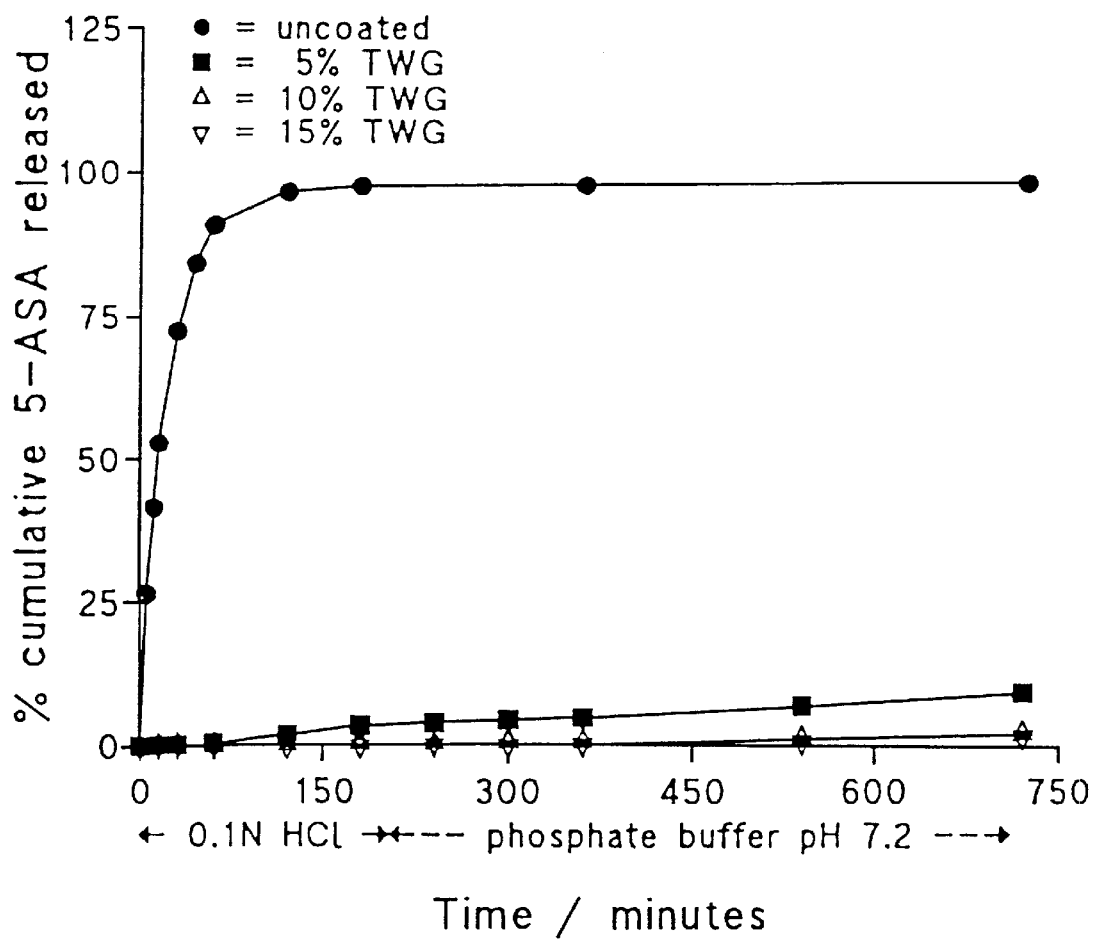

This 'acid' pre-treatment appeared to have the effect of strengthening the coats formed prior to their exposure to the simulated colonic medium Results of the Dissolution Tests (1) Effect of Coat Thickness on the Dissolution Profile of 5-ASA in Mixed Acid/Phosphate Buffer (a) Surelease®/Amylose System The effect of varying coat thickness for Surelease® to amylose ratios of 2.5: 1; 5:1; 7:1 and 10:1 was investigated. Results are shown for the ratios of 2.5:1 and 5:1 only in FIGS. 1 and 2 as the effect of thickness on the dissolution profile was small above a Surelease®:amylose ratio of 5:1. As the coat thickness increased from 5% TWG to 15% TWG the amount of 5-ASA released in dissolution tests decreased. The effect of thickness was most noticeable when the Surelease® to amylose ratio was lowest (2.5:1).

(b) Aquacoat®/Amylose System

The results were similar to those obtained for the Surelease®/Amylose system. As the thickness of the coat increased from 5% TWG to 15% TWG the amount of 5-ASA released in dissolution studies decreased.

Figure 3:
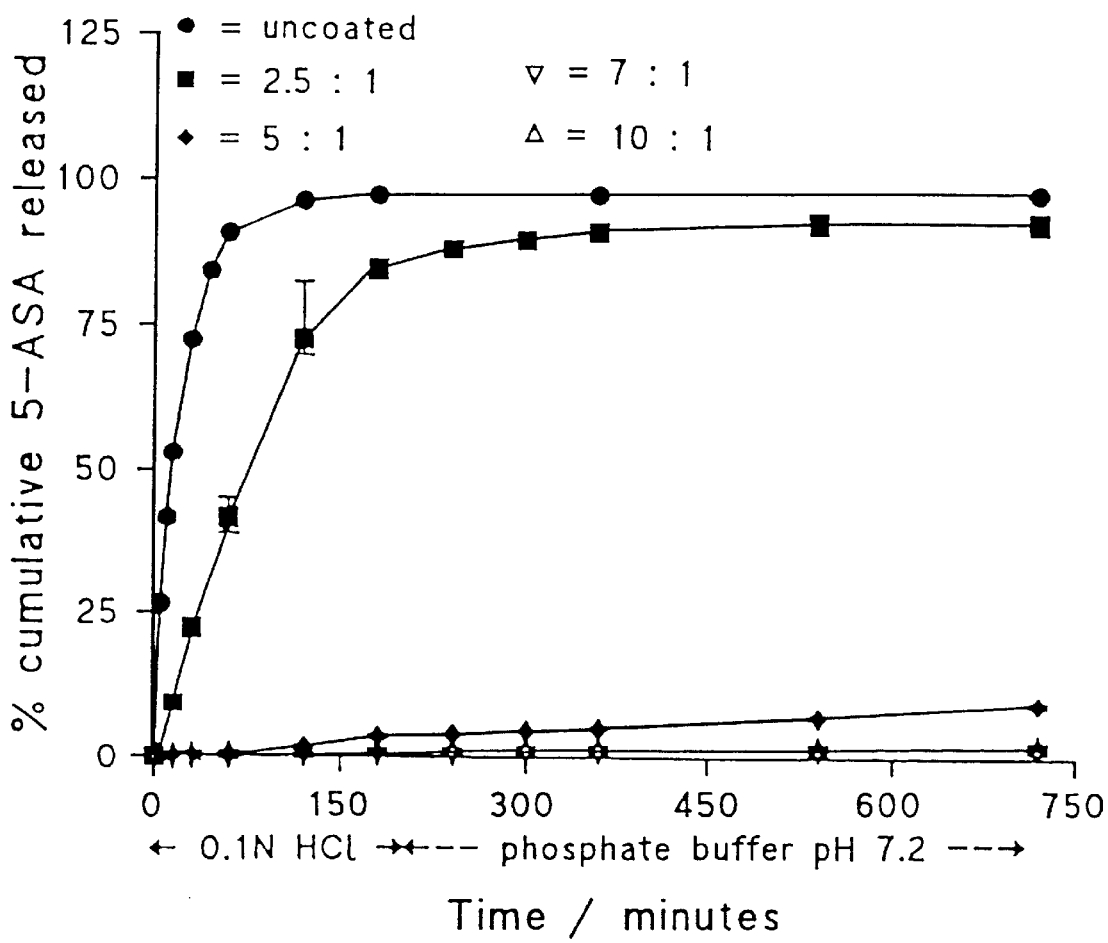

(2) Effect of the Ratio of Insoluble Polymer to Amylose on the Dissolution Profile of 5-ASA in Mixed Acid/Phosphate Buffer (a) Surelease®/Amylose System The effect of varying the ratio of Surelease® to amylose from 2.5:1 to 10:1 for a constant coat thickness of 5% TWG was investigated. As the ratio of Surelease® to amylose was increased, dissolution was retarded, the amount of 5-ASA released being decreased. The results are shown in FIG. 3 for a coat thickness of 5% TWG. The dissolution was severely retarded at Surelease®:amylose ratios of greater than 5:1. Similar results were obtained by repeating the experiment using coating thicknesses of TWG 10% and 15%. The results obtained confirmed the above findings that by increasing coat thickness, the release of 5-ASA was also retarded.

(b) Aquacoa®t/Amylose System

The results are similar to those obtained for the Surelease®/Amylose system. As the proportion of insoluble polymer (Aquacoat®) increased the amount of 5-ASA released in the dissolution test decreased.

Figure 4:
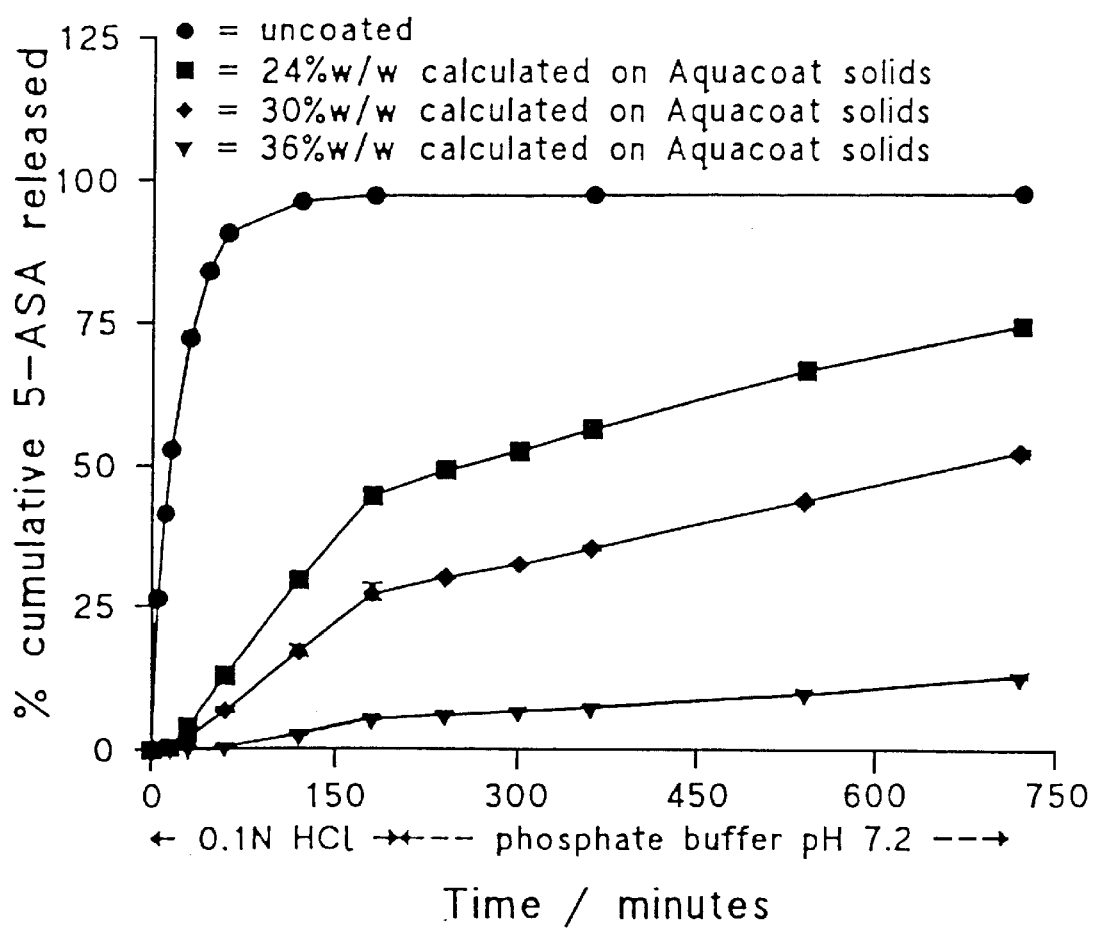

(3) Effect of the Proportion of Plasticiser on the Dissolution Profile of 5-ASA in Mixed Acid/Phosphate Buffer (a) Aquacoat®/Amylose System Commercially available Aquacoat® does not contain any additional plasticiser. The addition, therefore, of between 24% and 36% w/w of dibutyl sebacate plasticiser to coatings having coat thicknesses of 5%, 10% and 15% TWG and insoluble polymer to amylose ratios of 5:1, 7:1 and 10:1 were investigated. The results are shown in FIG. 4 for TWG 10% and Aquacoat®:amylose ratio of 5:1. Similar results were obtained for the other coating formulations investigated. From these results it is evident that as the quantity of dibutyl sebacate (DBS) plasticiser increased from 24% w/w to 36% w/w (calculated on the Aquacoat® solids) the amount of drug release decreased.

(b) Surelease®/Amylose System

Similar to results to those described for the Aquacoat®/ amylose system were obtained. In this case, the addition of between 0 and 12% of plasticiser by weight of ethyl cellulose polymer was added as commercially available Surelease® already contains 24% of a plasticiser.

Figure 5:
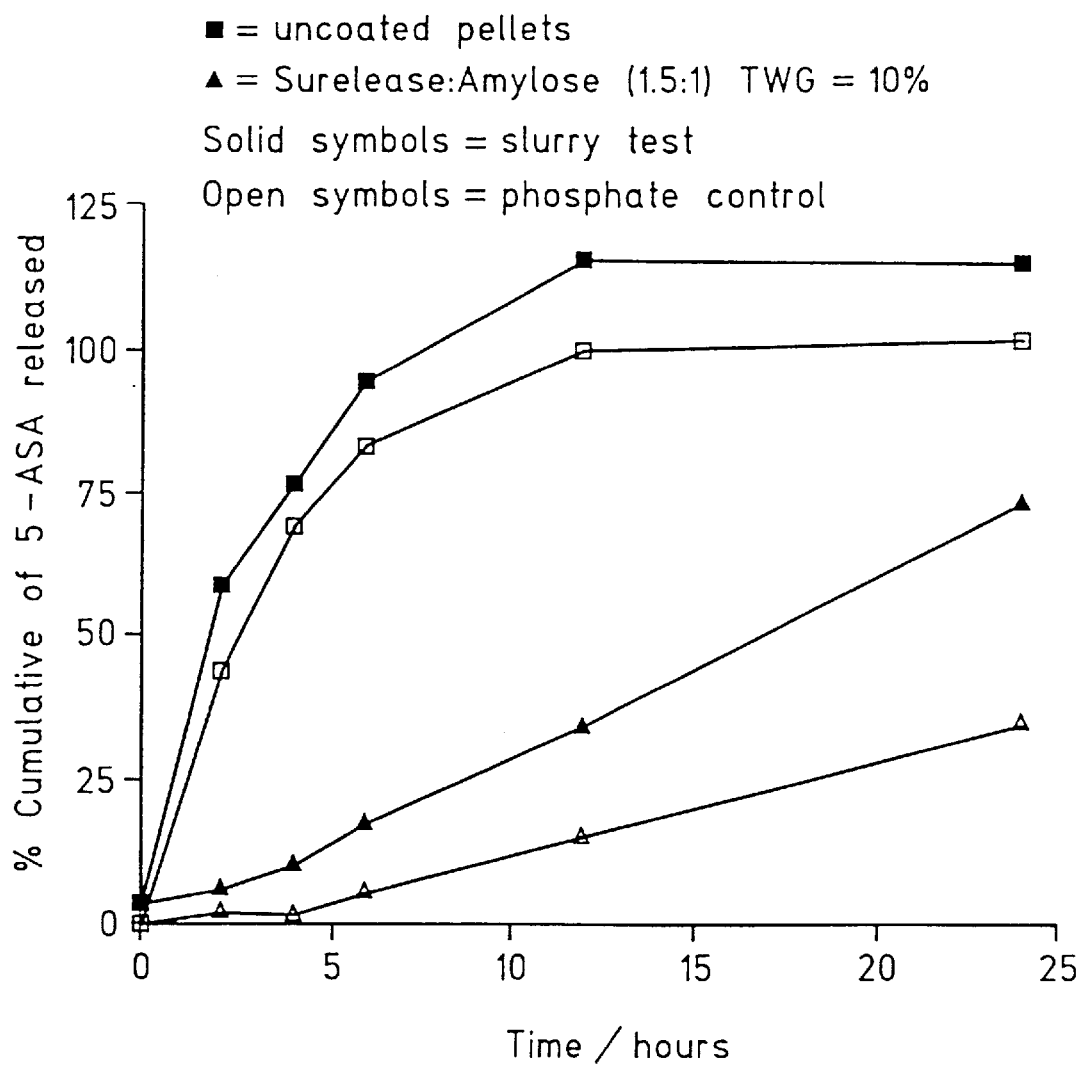

(4) Effect of Ratio of Insoluble Polymer to Amylose on the Specific Release of 5-ASA from Coated Pellets in the In Vitro Fermentation System (a) Surelease®/Amylose System Coatings formulations having Surelease®:amylose ratios of 1:1, 1.5:1, 2:1, 3:1 and 4:1 and coat thicknesses of 5%, 10% and 15% TWG were investigated. In FIG. 5 the specific release for a coating having a Surelease®:amylose ratio of 1.5:1 and 10% TWG is illustrated. Similar results were obtained from the other coating formulations. In general the rate of 5-ASA release was inhibited as the proportion of Surelease® in the formulation increased.

Pellets coated with Surelease®:amylose (1.5:1)+4% DBS, TWG=10% showed a much higher release in the faecal test compound compared to the phosphate control. Compositions with a Surelease®:amylose ratio of less than 2:1 were observed to give some release within the first 5 hours of the test.

(b) Aquacoat®/Amylose System

The results for this system are broadly similar to those for the Surelease®/amylose system. Pellets coated with Aquacoat®:amylose (2:1)+36% DBS, TWG=10% showed the optimum balance of minimal premature drug release in the upper gastro-intestinal tract with sufficiently large drug release in the colon.

For both systems the optimum conditions were found for those coatings having a sufficient ratio of amylose to allow easy digestion thereof without greatly compromising on premature release. These conditions appeared to be satisfied with Surelease®:amylose ratios of 1.5:1 and 2:1 respectively and with Aquacoat®:amylose (2:1)+36% DBS, TWG=10%.

(5) Glucose Release

Figure 6:
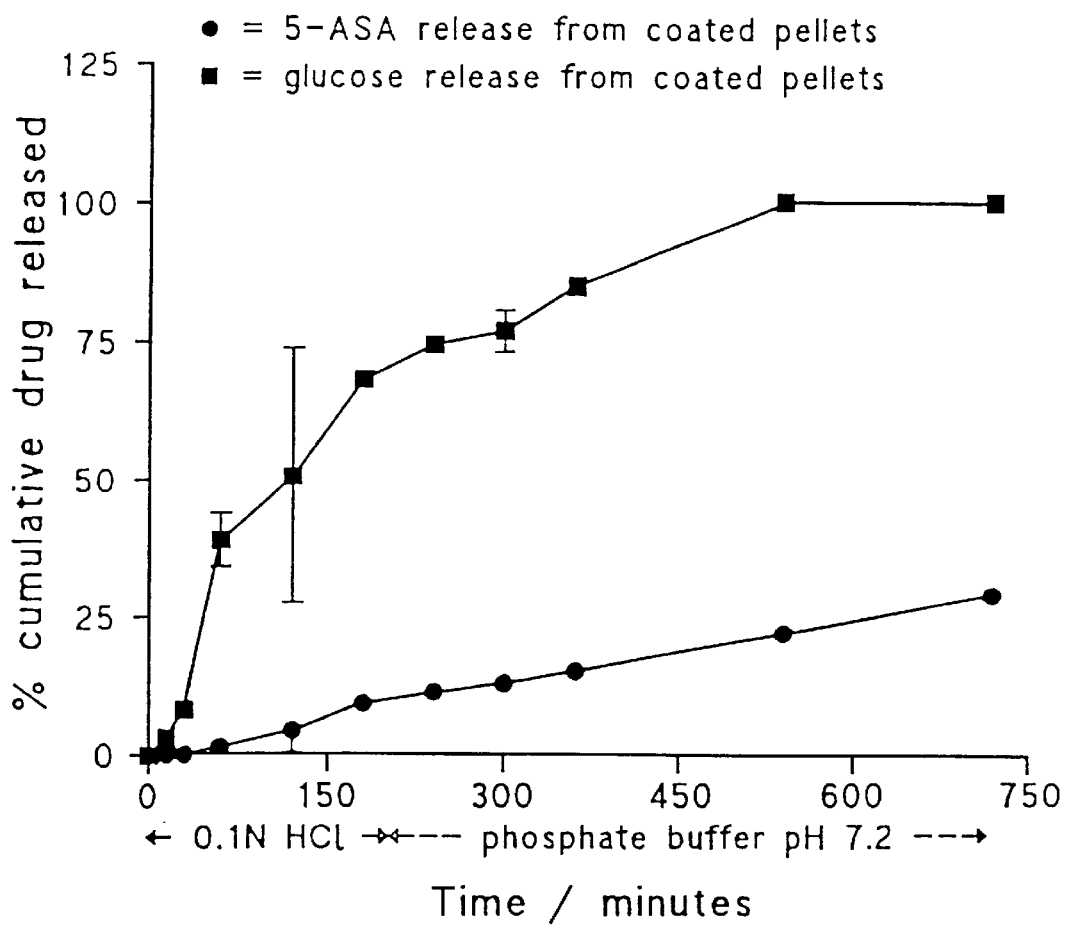

The release of glucose from pellets coated with Surelease®:amylose (1.5:1)+4% DBS, TWG=10% was observed to be significantly greater than the release of 5-ASA under the same conditions (FIG. 6). Similar results were obtained for pellets coated with Aquacoat®:amylose (2:1)+36% DBS, TWG=10%. Glucose is more soluble than 5-ASA. This suggests that the coating composition is more suitable for controlling the release of less soluble materials. Colonic delivery of orally administrable formulations comprising a moderate to highly water soluble active ingredient would require either the formation of thick coats, the use of film-forming compositions having a higher insoluble polymer to amylose ratio or a combination of both.

EXAMPLE 5

Stability Studies

Stability studies were conducted in controlled relative humidity conditions using chemicals from Merck, UK.

(a) Silica gel, technical grade, Merck, U.K. Batch No. 7019980N (b) Potassium carbonate, general purpose reagent grade, Merck, U.K. Batch No K21928435530

(c) Sodium nitrite, AnalaR grade, Merck, U.K. Batch No. C216466502

Formulations comprising coatings having Aquacoat® to amylose ratios of 5:1, 7:1 and 10:1;coat thicknesses of 5, 10 and 15% TWG and 24,30 and 36% of plasticiser by weight of the ethyl cellulose solids used in the aqueous dispersion were investigated for their stability to storage at 20° C. at 0% relative humidity (RH), 44% RH and 78% RH Results By varying the coat thickness of a given formulation, it was shown that the thinnest coat, 5% was unstable on 1 month storage at 20° C., 0% and 44% RH but stable at 20° C., 78% RH. On the other hand, coat thicknesses of 10% and 15% were shown to be stable at all the investigated storage conditions. Coat thickness had an influence on the coat stability. Formulations having a thicker coat were found to be more stable on storage.

By varying the quantity of plasticiser within a given formulation, it was shown that this variable also influenced coat stability. The influence of plasticiser was most marked at low humidity, the formulations being more stable when store under conditions of high relative humidity.

When the ratio of ethyl cellulose to amylose was varied from 5:1 to 10:1 the coat was stable only when stored at relative humidity of 44% and above.

Dosage formulations containing 5-ASA as the active ingredient were formed by coating 5-ASA pellet cores with a film-forming composition comprising Surelease® containing varying amounts of additional DBS, 0%, 4%, 8% and 12%. Dissolution results immediately after coating showed that there was little difference between the coats formed from the four formulations in terms of drug release. However, upon storage at ambient temperature and humidity, for one month, only formulations containing additional plasticiser were found to be stable. As little as 4% additional plasticiser was shown to be sufficient. As with the Aquacoat®/Amylose system, greater stability was observed when the formulations were stored under conditions of 44% RH and above.

What is claimed is:

1. A method of coating an active material or a dosage form containing an active material which coating retains the active material during passage through the gastro-intestinal tract and releases it in the colon, said method comprising contacting the active material or dosage form containing it at a temperature of less than 60° C. with a film-forming composition comprising an aqueous dispersion of an amylose-alcohol complex, an insoluble film-forming polymer and a plasticiser, coating being carried out at a temperature less than 60° C.

2. A method of coating a temperature sensitive active material or a dosage form containing such an active material which coating retains the active material during passage through the gastro-intestinal tract and releases it in the colon, said method comprising contacting the active material or dosage form containing it at a temperature less than 60° C. with a film-forming composition comprising an aqueous dispersion of an amylose-alcohol complex, an insoluble film-forming polymer and a plasticiser, coating being carried out at a temperature which is less than 60° C. and at which the integrity of the active material is maintained during the coating step.

3. A method according to claim 1 or 2, in which the coating temperature is less than 50° C.

4. A method according to claim 1 or 2, in which the coating temperature is between 30° C. and 40° C.

5. A method according to claim 1 or 2, in which the amylose alcohol complex is a complex of amylose and a $C_{3-6}$ alcohol.

6. A method according to claim 5, in which the amylose alcohol complex is a complex of amylose and butan-1-ol.

7. A method according to claim 1 or 2, in which the amylose has a molecular weight of at least 20,000.

8. A method according to claim 1 or 2, in which the amylose alcohol complex comprises from 1% to 12% by weight of the dispersion.

9. A method according to claim 1 or 2, in which the film-forming composition contains between 7 and 30% by weight of the insoluble, film-forming polymer.

10. A method according to claim 1 or 2, in which the film-forming composition contains between 20 and 40% of the plasticiser by weight of the insoluble, film-forming polymer.

11. A method according to claim 1 or 2, in which the ratio of insoluble, film-forming polymer to amylose-alcohol complex in the film-forming composition is from 1:1 to 7:1.

12. A method according to claim 11, in which the ratio is from 1:1 to 5:1.

13. A method according to claim 1 or 2, in which the film-forming composition contains from 4 to 8 % by weight of an amylose butanol complex formed from an amylose of molecular weight from 100,000 to 500,000 daltons, from 17 to 28% by weight of a film-forming cellulosic polymer, an acrylic polymer, or shellac, and from 24 to 36% of the plasticiser based on the weight of the film-forming polymer, coating being carried out at a temperature of from 30 to 40° C.

14. A method according to claim 13, in which the coated preparation is dried at a temperature of from 5 to 40° C. for up to 2 hours.

15. A dosage form of an active material, said dosage form being coated or containing active material coated according to the method of claim 1 or 2.

16. A dosage form of an active material, said dosage form being coated or containing active material coated according to the method of claim 14.

17. A method of treating a patient having a disorder of the colon or a disorder the treatment of which is best effected via the colon, comprising the oral administration thereto of a coated active material, or a coated dosage form containing the active material, prepared according to claim 1 or 2.

* * * * *